United States Patent [19]

Chu

[11] 4,404,123
[45] Sep. 13, 1983

[54] CATALYSTS FOR PARA-ETHYLTOLUENE DEHYDROGENATION

[75] Inventor: Chin-Chiun Chu, North Brunswick, N.J.

[73] Assignee: Mobil Oil Corporation, New York, N.Y.

[21] Appl. No.: 449,913

[22] Filed: Dec. 15, 1982

[51] Int. Cl.$^3$ .......................... B01J 23/08; B01J 23/16
[52] U.S. Cl. ................................... 252/463; 252/465; 252/470; 252/474; 585/445
[58] Field of Search ............... 252/465, 463, 470, 474; 585/445

[56] References Cited

U.S. PATENT DOCUMENTS

| | | | |
|---|---|---|---|
| 1,935,177 | 11/1933 | Connolly et al. | 252/463 |
| 2,206,773 | 7/1940 | Hale | 252/474 |
| 2,775,637 | 12/1956 | Lanning et al. | 252/474 |
| 3,338,952 | 8/1967 | Callahan | 252/470 |
| 3,409,688 | 11/1968 | Pan | 252/474 |
| 3,887,495 | 6/1975 | Juguin et al. | 252/463 |
| 4,001,317 | 1/1977 | Groselli et al. | 252/470 |
| 4,052,450 | 10/1977 | Krabetz et al. | 252/465 |
| 4,101,448 | 7/1978 | Shaw et al. | 252/465 |
| 4,143,083 | 3/1979 | Riesser | 252/470 |
| 4,144,197 | 3/1979 | Riesser | 585/445 |
| 4,162,234 | 7/1979 | Grasselli et al. | 252/470 |
| 4,329,517 | 5/1982 | Tamguchi et al. | 252/463 |

Primary Examiner—Delbert E. Gantz
Assistant Examiner—Cynthia A. Prezlock
Attorney, Agent, or Firm—Alexander J. McKillop; James F. Powers, Jr.; Edward F. Kenehan, Jr.

[57] ABSTRACT

Para-ethyltoluene dehydrogenation catalyst compositions and processes for using such catalysts are provided. The catalyst compositions comprise a catalytically active iron compound, e.g., iron oxide; a potassium catalyst promoter, e.g., potassium carbonate; an optional chromium compound stabilizer, e.g., chromic oxide, and a gallium compound, e.g., gallium trioxide. Utilization of particular amounts of gallium compound in dehydrogenation catalyst compositions of this type will provide a catalyst especially suitable for promoting the selective dehydrogenation of para-ethyltoluene to form para-methylstyrene with sustained catalyst activity, with minimized aromatic ring loss and with minimal formation of popcorn polymer from the reaction effluent.

4 Claims, No Drawings

CATALYSTS FOR PARA-ETHYLTOLUENE DEHYDROGENATION

BACKGROUND OF THE INVENTION

1. Field of the Invention

This invention relates to improved catalysts for the selective dehydrogenation of dialkyl aromatic hydrocarbons to produce alkyl vinyl aromatic hydrocarbons, more particularly to catalysts for the production of para-methylstyrene (PMS) via the dehydrogenation of para-ethyltoluene (PET).

2. The Prior Art

The vinyl benzenes play a particularly important role in the preparation of synthetic plastics and resins. The polymerization of styrenes, for example, to produce polystyrene resins is well known.

Styrene and styrene derivatives are typically produced from ethylbenzene materials by dehydrogenation over solid catalysts in the presence of co-fed steam, and at temperatures ranging from 500° to 700° C. The catalysts found to be the most effective for this process are those which are based on potassium oxide (carbonate) promoted, chromium oxide stabilized, iron oxide material. Catalysts of this type are said to be self-regenerative inasmuch as, in addition to their effectivness in promoting dehydrogenation, they also promote the water gas reaction in the presence of the steam co-feed, to thereby remove coke which would otherwise build up on and deactivate the catalyst. The lifetime of such self-regenerative catalysts is thus determined by the effectiveness of the catalyst in maintaining its activity for conversion of ethylbenzene materials such as para-ethyltoluene for any given steam/hydrocarbon ratio in the feed. Catalysts of this type which can maintain such activity at generally lower steam/hydrocarbon ratios are, of course, more economically desirable.

Another problem which can diminish the economical production of certain styrene derivatives such as p-methylstyrene via the steam dehydrogenation of p-ethyltoluene is the problem of "popcorn" polymer formation. Popcorn polymers are those solid polymeric materials which are popcorn-like in appearance and which can form and build up at the relatively cooler exit port of the dehydrogenation reaction reactor vessel and in the condenser and other parts of the cooling train used to recover dehydrogenation products. Popcorn polymer formation does not generally occur when ethylbenzene is dehydrogenated but can be a significant problem during dehydrogenation of para-ethyltoluene. While various inhibitors can be added to the dehydrogenation reactor effluent to minimize popcorn polymer formation, the eventual buildup of such materials can necessitate shutdown of the dehydrogenation reaction equipment to remove the accummulated popcorn polymer. Obviously, dehydrogenation catalysts which reduce the inherent tendency of popcorn polymers to form in the dehydrogenation reaction effluent would be economically attractive for commercial scale production of styrenic materials.

Yet another problem which can occur when styrene derivatives such as p-methylstyrene are prepared from ethyltoluene materials by dehydrogenation over catalysts of the type herein involved is the phenomenon of aromatic ring loss. The catalyst employed to effect conversion of the ethyltoluene materials can to some extent also promote cracking of the ring structures of the aromatic reactants and products. Obviously it is desirable to identify those catalytic materials which minimize the amount of aromatic ring loss during the dehydrogenation reaction while maintaining high conversion of ethyltoluene to p-methylstyrene.

In view of the foregoing considerations, there is clearly a continuing need to formulate steam regenerative dehydrogenation catalysts suitable for promoting production of particular styrenic materials from substituted ethylbenzene materials, e.g., selective production of p-methylstyrene from p-ethyltoluene, with improved catalyst lifetimes, especially at lower steam/hydrocarbon ratios in the reactor feed, with minimized propensity of the reaction effluent to form popcorn polymer, and with minimized loss of aromatic ring structure during the reaction.

Accordingly, it is an object of the present invention to provide an improved iron oxide based, steam-regenerative dehydrogenation catalyst especially useful for the dehydrogenation of para-ethyltoluene to selectively produce para-methylstyrene.

It is a further object of the present invention to provide such dehydrogenation catalysts having extended catalyst lifetime, with acceptable activity for low ring loss conversion of p-ethyltoluene and with desirably high selectivity to production of p-methylstyrene, even at low steam/hydrocarbon ratios in the charge to the reaction zone.

It is a further object of the present invention to provide such a catalyst which produces a p-methylstyrene-containing dehydrogenation reaction effluent having minimized tendency to form solid "popcorn" polymer.

It is a further object of the present invention to provide a low aromatic ring loss para-ethyltoluene dehydrogenation process employing a catalyst having extended lifetime with minimal tendency of the dehydrogenation reaction effluent to form popcorn polymer.

These and other objectives can be achieved by means of the invention described and claimed herein.

SUMMARY OF THE INVENTION

The present invention relates to an improved dehydrogenation catalyst composition especially useful for the selective dehydrogenation of para-ethyltoluene to produce para-methylstyrene. Such a catalyst comprises from about 30% to 60% by weight of an iron oxide component, calculated as ferric oxide, from about 13% to 48% by weight of a potassium compound component, calculated as potassium oxide, from about 0% to about 5% by weight of a chromium compound component, calculated as chromic oxide, and from about 1% to 15% by weight of a gallium compound calculated as gallium trioxide.

The present invention also relates to a dehydrogenation process wherein para-ethyltoluene, along with steam, is passed over this gallium-containing catalyst composition at a temperature from about 500° C. to 700° C. with a LHSV of from about 0.3 to 3, and a steam to hydrocarbon weight ratio of from about 1:1 to 5:1, to selectively produce para-methylstyrene with extended catalyst lifetime, with minimized aromatic ring loss and with minimized formation of popcorn polymer in the dehydrogenation effluent.

DETAILED DESCRIPTION OF THE INVENTION

The dehydrogenation catalyst compositions of the present invention contain as an essential catalytic component one or more iron compounds, generally in the form of iron oxide. Many forms of iron oxide can be used in the catalyst compositions of this invention. Typically, iron oxides employed in catalyst preparations of this sort are a synthetically produced, powdered red, red-brown, yellow or black pigment. The red or red-brown pigments are highly pure ferric oxide, while the black pigment is the magnetic form, ferrosoferric oxide ($Fe_3O_4$), which is usually found in the catalyst under various reaction conditions. The yellow iron oxides consist of the monohydrated form of ferric oxide. These oxides are prepared by various methods, e.g., oxidation of iron compounds, roasting, precipitation, calcination, etc. A suitable form of iron compound is the monohydrated yellow iron oxide used in the preparation of catalysts according to U.S. Pat. Nos. 3,360,597, issued Dec. 26, 1967, and 3,364,277; issued Jan. 16, 1968. Particularly suitable are pigment grade red iron oxides of purities exceeding 98% weight. These red oxides have surface areas ranging from 2 to 50 $m^2$/gram and particle sizes from 0.1 to 2 microns. The iron compound is present in the catalyst in either one or a mixture of both of its possible oxidation states, i.e., as ferrous iron of ferric iron or mixtures thereof, as for example, ferrosoferric iron.

The catalyst compositions herein generally comprise from about 30% to 60% by weight, preferably from about 35% to 55% by weight, of iron oxide calculated as ferric oxide. Alternatively stated, the catalyst compositions herein generally comprise from about 21% to 42% by weight, and preferably from about 24% to 39% by weight, of iron oxide, calculated as iron metal.

The dehydrogenation catalyst compositions of the present invention also essentially comprise, as a catalyst promoter, one or more potassium compounds. The potassium promoter material can be added to the catalyst in various forms. For example, it may be added as the oxide, or as other compounds which are convertible, at least in part, under calcination conditions, to the oxides, such as the hydroxides, the carbonates, the bicarbonates, the phosphates, the borates, the acetates, and the like. A particularly preferred potassium compound is potassium carbonate. The potassium compound is generally present in the catalyst as a potassium oxide, a potassium carbonate or a mixture thereof. High carbon dioxide partial pressures in the reaction gases will favor high carbonate to oxide ratios and vice versa within the potassium component.

The catalyst compositions herein generally comprise from about 13% to 48% by weight, and preferably from about 27% to 41% by weight, of potassium promoter compound, calculated as potassium oxide. Alternatively stated, the catalyst compositions herein generally contain from about 11% to 40% by weight, and preferably from about 22% to 34% by weight, of potassium oxide, calculated as potassium metal.

An optional, but frequently utilized, third component of the present catalyst composition is a chromium compound which serves as a stabilizer for the active catalytic components. Chromium compounds have, in fact, typically been added to alkali-promoted iron oxide catalysts to extend their life. Chromium, as used in the compositions of this invention, can be added to the catalyst in the form of a chromium oxide or in the form of chromium compounds which decompose upon calcination to chromium oxides, as for example, chromium nitrates, hydroxides, acetates, and the like. Chromium can also be added in the form of alkali metal chromates. If potassium chromates are used, such materials can, of course, also contribute to the requisite concentration of potassium essentially present in the dehydrogenation catalyst compositions as hereinbefore discussed.

Thus, the catalyst compositions herein can comprise from about 0% to about 5% by weight, and preferably from about 1% to 4% by weight chromium compound, calculated as chromic oxide. Alternatively stated, the present composition can comprise from about 0% to 3.5% by weight, preferably from about 1.4% to 2.8% by weight, of a chromium oxide calculated as chromium metal.

In accordance with the present invention, the dehydrogenation catalyst compositions containing iron, potassium and optionally chromium compounds, as described, also essentially contain particular selected amounts of a gallium compound which can provide gallium trioxide in the catalyst compositions herein, e.g., after calcination. Addition of gallium compounds to the particular iron-potassium-chromium dehydrogenation catalysts utilized herein serves to enhance catalyst lifetime when such catalyst compositions are used to promote the preferential formation of para-methylstyrene from para-ethyltoluene with low aromatic ring loss, especially at steam/hydrocarbon ratios below about 2:1. It has also been surprisingly discovered that the para-methylstyrene containing dehydrogenation reaction effluent is especially resistant to the subsequent formation of "popcorn" polymers of methylstyrene when the dehydrogenation reaction has been conducted over the particular gallium trioxide-containing catalysts of the present invention.

Gallium as used in the catalyst compositions of the present invention can be added to the catalyst in the form of gallium trioxide $Ga_2O_3$, or in the form of other gallium compounds which decompse upon calcination to form gallium trioxide, as for example, the hydroxide, nitrate, acetate and oxalate compounds of gallium. Gallium trioxide itself is a stable solid material which, like alumina, can exist in several crystalline forms. $\beta$-$Ga_2O_3$ is the form most commonly encountered and is the form of gallium trioxide which is preferred for use herein. Gallium compounds are added to the catalyst compositions of the present invention to the extent of from about 1% to 15% by weight, more preferably from about 2% to 10% by weight, calculated as $Ga_2O_3$.

In addition to the foregoing materials, the catalyst compositions of the present invention can optionally contain a wide variety of materials suitable for altering, adjusting or modifying the catalytic and/or physical properties of such compositions. Materials, for example, which can act as stabilizers, activators, and promoters for dehydrogenation catalysts of the type herein contemplated include, cobalt, cadmium, aluminum, nickel, cesium, and rare earths. Such additives can be incorporated in various forms including their elemental form or in the form of their oxides. If employed, such stabilizers, activators and/or promoters generally comprise from about 1% to 15% by weight of the catalyst compositions herein.

The physical strength of the catalyst compositions of the present invention can be improved, if desired, by adding any of a variety of optional binding agents. Binding agents can include, for example, calcium aluminate and portland cement. The density of the catalyst compositions herein can likewise be modified by the addition of various filler substances, for example, combustible materials such as sawdust, carbon, wood flour, etc.

Such materials can be added to the compositions during preparation and thereafter burned out after the catalyst pellets have been formed. Other porosity promoting aids include graphite and aqueous solutions of methylcelluose, which also facilitate extrusion of catalyst pellets as hereinafter described. If employed, binders and other fillers generally comprise up to about 20% by weight of the catalyst composition.

The catalyst compositions of the present invention are in general prepared by admixing the essential and desired optional components as hereinbefore described and by thereafter drying and optionally calcining the resulting mixture. Calcination temperatures can range from about 100° C. to 600° C., preferably from about 150° C. to 550° C. The compounds of the catalyst compositions herein can be admixed in various ways. One method comprises ballmilling together a mixture of the desired oxides and/or compounds decomposable upon calcination to oxides, adding a small amount of water, and extruding the paste formed to produce small pellets, which are then dried and calcined. Another method is to dissolve the components together, spray dry these components to form a resulting powder, calcine the powder into the resultant oxides, and then add sufficient water to form a paste which is extruded into pellets, dried and calcined. Another procedure involves precipitating those materials which are precipitatable, such as iron, chromium and gallium, as the resultant hydroxides, partially dewatering the resultant precipitate, adding soluble salts of the other required metals, and then subsequently extruding, drying and calcining the resulting pellets. A preferred method involves dry-blend powdering of oxides and/or compounds decomposable upon calcination to the oxides, adding water, optionally containing dissolved therein soluble compounds decomposable upon calcination to the oxides, then mixing and/or mulling the resultant paste, pelletizing the mixture, subsequently substantially drying at a temperature from about 50° C. to about 300° C., followed by calcining the pellets to form the final product. The drying and calcining could be carried out stepwise in the same furnace by suitable programming of the furnace temperature. Alternatively, water-insoluble dry powders of oxides and/or compounds decomposable upon calcination to the oxides are dry-mixed, and the balance of the other materials needed are dissolved in water and the resultant solution is used to form the paste with the dry powders. There are many variations of the mixing of dry powders, water and water soluble compounds that give equivalent results and fall within the scope of this invention.

The catalysts of the present invention are especially effective in promoting the dehydrogenation of para-ethyltoluene to selectively produce para-methylstyrene. Such a dehydrogenation reaction is usually carried out at reaction temperatures of about 500° C.–700° C. However, higher or lower temperatures may be used without departing from the scope of this invention. The use of atmospheric, sub-atmospheric, or super-atmospheric pressure is suitable. However, it is preferable to operate at as low a pressure as is feasible, and atmospheric or sub-atmospheric pressure is preferred. The process of the invention may be carried out in batch, semi-continuous, or continuous operation, with continuous operation being preferred. The catalyst is employed in the form of a fixed bed, or in fluidized or suspended form. It is preferable to utilize a fixed bed. The reaction may be carried out in single stage reactors or by staging in series reactors. The reactors may be of various designs, e.g., downflow reactors, radial reactors, etc.

With the use of the catalyst of this invention, it is essential to add steam to the reactant feed to promote the removal of carbonaceous residues from the catalyst. The reaction feed generally contains from 2–30 moles of steam for every mole of organic feed. Catalysts having higher potassium contents are usually employed at lower steam to feed ratios. Steam to hydrocarbon weight ratios in the feed of from about 1:1 to about 5:1 can be employed. Good results and extended catalyst lifetimes can be obtained with steam to hydrocarbon weight ratios of about 1.5:1 to about 4:1.

The contact time of the reactant-containing gas hydrocarbon with the catalyst is usually defined in terms of liquid-hourly-space velocity (volume of liquid hydrocarbon reactant per volume of catalyst per hour, i.e., LHSV). The hydrocarbon LHSV according to this invention may vary from about 0.3 to 3 and is preferably adjusted within this range to effect the degree of conversion desired for the particular feed in question.

The catalysts of the present invention and their use will be further described by the following illustrative examples which are provided for illustration and are not to be construed as limiting the invention.

EXAMPLE I

A reference dehydrogenation catalyst is formulated by admixing the following materials in the following concentrations:

| COMPONENT | CONCENTRATION (WT %) |
|---|---|
| $Fe_2O_3$ | 46% |
| $K_2CO_3$ | 51% |
| $Cr_2O_3$ | 3% |
| | 100.0% |

To this mixture is added water to the extent of 20% and the resulting mixture is formed into a paste. The paste is formed into a ⅜" disk which is dried for at 180° C. for 16 hours and thereafter crushed to 5–8 mesh.

EXAMPLE II

The dehydrogenation catalyst prepared as in Example I is used to dehydrogenate para-ethyltoluene (PET) at atmospheric conditions to form para-methylstyrene (PMS) in a tubular reactor maintained at 620° C. to which PET and steam are introduced. Feed rates are varied for two such dehydrogenation runs. Feed rates and the resulting conversion of p-ethyltoluene and selectivity to production of p-methylstyrene are set forth in Table I:

TABLE I

| | | | | Conversion Results | |
|---|---|---|---|---|---|
| | \multicolumn{2}{c}{Feed Rates (LHSV)} | | | Para- |
| Run No. | PET | Water | $H_2O$/ Hydrocarbon Weight Ratio | PET Conversion (Mole %) | Methylstyrene Selectivity (Mole %) |
| 1 | 1.0 | 1.6 | 1.85:1 | 61.4 | 89.9 |
| 2 | 0.4 | 0.64 | 1.85:1 | 65.2 | 87.2 |

Dehydrogenation of Para-Ethyltoluene (PET) Over Reference Catalyst

In carrying out such a reaction it was noted that, after several hours on stream, the exit port of the reactor and condenser used to recover the reaction products plugged up due to formation of "popcorn" polymer therein. To prevent such polymer formation, H₂S was added at a rate ranging from 1 to 4 cc per minute of H₂S (gas) per 100 ml per hour of PET (liquid) at the exit port of the tubular reactor.

EXAMPLE III

In a manner similar to that set forth in Example I, another dehydrogenation catalyst is prepared. The following dry materials are admixed in the concentrations shown.

| Component | Concentration (wt. %) |
|---|---|
| Fe₂O₃ | 44.2 |
| K₂CO₃ | 49.0 |
| Cr₂O₃ | 2.9 |
| Ga₂O₃ | 3.9 |
| | 100.0% |

Water is added to the extent of 20% and the resulting paste is again shaped into a ⅜″ disk, dried at 180° C. for 16 hours and then crushed to 5-8 mesh. The resulting Ga₂O₃-containing catalyst composition contains the same ratio of iron oxide to potassium carbonate to chromic oxide as does the reference catalyst of Example I.

EXAMPLE IV

Using the Ga₂O₃-containing catalyst of Example III and the general reaction conditions of Example II, para-ethyltoluene (PET) is again dehydrogenated to para-methylstyrene (PMS). The conversion results are set forth in Table II:

TABLE II

Dehydrogenation of Para-Ethyltoluene (PET) Over Gallium Trioxide-Containing Catalyst

| | | | Conversion Results | |
|---|---|---|---|---|
| Run No. | Feed Rates (LHSV) PET | Water | H₂O/ Hydrocarbon Weight Ratio | PET Conversion (Mole %) | Para-Methylstyrene Selectivity (Mole %) |
| 3 | 1 | 1.6 | 1.85:1 | 57.4 | 90.5 |
| 4 | 0.4 | 0.64 | 1.85:1 | 63.3 | 88.2 |

Very little "popcorn" polymer forms in the reactor exit port or condenser during the runs over the Ga₂O₃-containing catalyst. Accordingly no H₂S inhibitor was added to the reactor effluent for runs lasting as long as 800 hours.

A comparison of the conversion results from Tables I and II shows that the Ga₂O₃-modified catalyst gives acceptable conversion of p-ethyltoluene with excellent catalyst selectivity to p-methylstyrene production. Such conversion further occurs with reduced propensity of the reaction effluent to form popcorn polymer.

EXAMPLE V

Using the same Ga₂O₃-containing catalyst of Example III, and the general reaction conditions of Example II, para-ethyltoluene (PET) is again steam dehydrogenated to para-methylstyrene (PMS) for an extended period of time. Using the feed rates and steam/hydrocarbon ratios set forth, conversion results after 14 days of operation are set forth in Table III.

TABLE III

Dehydrogenation of Para-Ethyltoluene (PET) Over Gallium Trioxide-Containing Catalyst

| | | | Conversion Results | |
|---|---|---|---|---|
| Run No. | Feed Rates (LHSV) PET | Water | H₂O/ Hydrocarbon Weight Ratio | PET Conversion (Mole %) | Para-Methylstyrene Selectivity (Mole %) |
| 5 | 1 | 1.40 | 1.7 | 54.8 | 90.5 |
| 6 | 1 | 1.35 | 1.55 | 50.9 | 90.4 |

The Table III data indicate that even after extended periods of time and at the H₂O/hydrocarbon ratios used, the gallium-containing catalyst of the present invention still provides acceptable conversion of para-ethyltoluene with excellent selectivity to production of para-methylstyrene.

EXAMPLE VI

Another catalyst sample is prepared in the same general manner as described in Example III. Such a sample also contains Fe₂O₃, K₂CO₃, Cr₂O₃ and Ga₂O₃ in approximately the same proportion as does the Example III catalyst. This new sample is also tested in the same general manner as described in Example II for its ability to promote dehydrogenation of para-ethyltoluene at various LHSV values and H₂O/PET ratios. Results of such testing are set forth in Table IV.

TABLE IV

Dehydrogenation of Para-Ethyltoluene (PET) Over Ga₂O₃-Containing Catalyst at 620° C.-Varying Conditions

| Run No. | PET LHSV | H₂O/PET (wt) | % PET Conversion | % PMS Selectivity | Ring Loss % |
|---|---|---|---|---|---|
| 1 | 1.0 | 2.0 | 57–60 | 90–91 | 0.3–0.45 |
| 2 | 1.0 | 1.85 | 56–58 | 90–91 | 0.4–0.5 |
| 3 | 1.0 | 1.7 | 54–55 | 90–91 | 0.45–0.6 |
| 4 | 1.0 | 1.55 | 49–50 | 90–91 | 0.5–0.7 |
| 5 | .6 | 2.0 | 60–62 | 88–89 | 0.5–0.7 |
| 6 | .6 | 1.85 | 58–60 | 88–89 | 0.6–0.8 |
| 7 | .4 | 1.85 | 61–64 | 87–88.5 | 0.8–1.1 |
| Reference catalyst of Example I - No Ga₂O₃ | .4 | 1.85 | 58–59 | — | 1.4–1.9 |

The Table IV data indicate that the catalysts of the present invention maintain PMS selectivity even at lower H₂O/PET ratios. Further the ring loss for the Ga₂O₃-containing catalyst is lower than with the Ga₂O₃-free catalysts at comparable or higher PET conversion levels. Very little "popcorn" polymer forms in the reactor effluent for the runs using the Ga₂O₃-containing catalyst.

What is claimed is:

1. A dehydrogenation catalyst composition especially suitable for promoting the dehydrogenation of para-ethyltoluene to selectively form para-methylstyrene, said catalyst composition comprising:
   a. from about 30% to 60% by weight of iron oxide, calculated as ferric oxide;
   b. from about 13% to 48% by weight of potassium compound, calculated as potassium oxide;
   c. from about 0% to 5% of chromium compound, calculated as chromic oxide; and
   d. from about 1% to 15% by weight of a gallium compound, calculated as gallium trioxide.

2. A composition in accordance with claim 1 wherein a. the iron oxide comprises from about 35% to 55% by weight of the composition;
b. the potassium compound comprises from about 27% to 41% by weight of the composition;
c. the chromium compound comprises from about 1% to 4% by weight of the composition; and
d. the gallium compound comprises from about 2% to 10% by weight of the composition.

3. A composition in accordance with claim 1 which additionally contains from about 1% to 15% by weight of modifying component selected from the group consisting of the elements cobalt, cadmium, aluminium, nickel, cesium, the rate earth metals and oxides of said elements.

4. A composition in accordance with claim 1 which additionally contains up to about 20% by weight of a binder/filler component selected from the group consisting of portland cement, calcium aluminate, sawdust, carbon, wood flour, graphite, methylcellulose and mixtures thereof.

* * * * *

UNITED STATES PATENT AND TRADEMARK OFFICE
CERTIFICATE OF CORRECTION

PATENT NO. : 4,404,123
DATED : September 13, 1983
INVENTOR(S) : Chin-Chium Chu

It is certified that error appears in the above—identified patent and that said Letters Patent is hereby corrected as shown below:

Col. 3, line 23, "of" should read --or--.

Col. 10, line 2 (Claim 3, line 5), "rate" should read --rare--.

Signed and Sealed this

Fourth Day of September 1984

[SEAL]

Attest:

GERALD J. MOSSINGHOFF

Attesting Officer

Commissioner of Patents and Trademarks